United States Patent [19]

Chao et al.

[11] Patent Number: 5,216,484
[45] Date of Patent: Jun. 1, 1993

[54] REAL-TIME IMAGING SPECTROMETER

[75] Inventors: Tien-Hsin Chao, Valencia; Li-Jen Cheng Cheng, LaCrescenta; Jeffrey W. Yu, Granada Hills; James L. Lambert, Sunland, all of Calif.

[73] Assignee: The United States of America as represented by the Administrator of the National Aeronautics and Space Administration, Washington, D.C.

[21] Appl. No.: 805,341

[22] Filed: Dec. 9, 1991

[51] Int. Cl.⁵ .............................................. G01J 3/12
[52] U.S. Cl. .................................. 356/326; 356/51; 250/339; 359/308
[58] Field of Search ............... 356/300, 308, 326, 328, 356/51; 359/308; 250/339

[56] References Cited

U.S. PATENT DOCUMENTS

| | | | |
|---|---|---|---|
| 4,490,845 | 12/1984 | Steinbruegge et al. | 250/343 |
| 4,622,845 | 11/1986 | Ryan et al. | 356/432 |
| 4,652,756 | 3/1987 | Ryan et al. | 359/308 |
| 4,663,961 | 5/1987 | Nelson et al. | 73/53 |
| 4,883,963 | 11/1989 | Kemeny et al. | 250/343 |

FOREIGN PATENT DOCUMENTS 0214129  12/1983  Japan ................................. 359/308

OTHER PUBLICATIONS

Gottlieb et al., SPIE, vol. 232, 1980, International Optical Computing Conference (1980) pp. 33–41.
Acoustooptic Devices and Applications by I. C. Chang, IEEE Transactions On Sonics and Ultrasonics, vol. su-23, No. 1, Jan. 1976.
Tunable Acousto-Optic Filters: An Overview by I. C. Chang, Optical Engineering, vol. 16, No. 5, Sep./Oct. 1977.
Acoustooptic Image Filtering by I. B. Belikov et al., Sov. Tech. Phys. Lett. 10(10), Oct. 1984.
Rapid Scanning Fluorescence Spectroscopy Using an Acousto-Optic Tunable Filter by Ira Kurtz et al., Rev. Sci. Instrum. 58(11), Nov. 1987.

Primary Examiner—F. L. Evans
Attorney, Agent, or Firm—John H. Kusmiss; Thomas H. Jones; Guy M. Miller

[57] ABSTRACT

An improved AOTF-based imaging spectrometer that has ability to electronically set the bandpass wavelength of an AOTF to any desired value in its wide tuning range, provides significant observational flexibility. This allows observations to be tailored in real-time and enables the spectrometer to address a wide range of objectives and permits real-time modification of the observational parameters, such as in flight or in other situations in which only remote control is possible. Various improvements in optical architecture provide simplified magnification variability, improved image resolution and light throughput efficiency and reduced sensitivity to ambient light. A preferred embodiment employs a camera zoom lens as the input lens. A TeO₂ AOTF and a relay lens are placed at selected distances behind the back focal plane of the input lens, respectively. A charge coupled device (CCD) camera, which comprises a camera, camera zoom lens and a CCD detector is placed at a selected distance behind the relay lens. An RF signal generator is used to drive the AOTF. Two embodiments of the invention are disclosed herein. One operates in the visible/near-infrared domain, in the wavelength range of 0.48 to 0.76 microns. The other operates in the infrared wavelength range of 1.2 to 2.5 microns.

16 Claims, 6 Drawing Sheets

REAL-TIME IMAGING SPECTROMETER

ORIGIN OF INVENTION

The invention described herein was made in the performance of work under a NASA contract, and is subject to the provisions of Public Law 96-517 (35 USC 202) in which the Contractor has elected not to retain title.

TECHNICAL FIELD

The present invention relates generally to the field of optical imaging systems and more specifically to an imaging spectrometer which may be used in space applications, such as for remote sensing, observation and sorting chores, but which also has applications in environmental monitoring, astronomy, industrial sorting, medical and military fields.

BACKGROUND ART

The airborne/spaceborne imaging spectrometer is an effective remote sensor for the earth sciences. There are two types of airborne multi-spectral imaging instruments. One uses a set of fixed wavelength bandpass filters to obtain spectral information. These instruments have provided a wealth of extremely useful information, but they suffer either from limited spectral coverage due to the limited number of filters that can be designed into a camera or from inadequate spectral resolution. The other type of instrument uses a scanning image technique with dispersive devices, such as diffraction gratings to provide spectral information. Some of these instruments can provide high spectral resolution observations. However images are composed later in the laboratory. Thus, the operation is not real-time. One notable example of this type of instrument is the Airborne Visible and Infrared Imaging Spectrometer (AVIRIS). There is therefore an ongoing need for an airborne/spaceborne imaging spectrometer which can operate in real-time and which does not require a large number of filters or suffer from inadequate spectral resolution. It will be seen hereinafter that the present invention overcomes these disadvantages and meets such a need by utilizing an acousto-optic tunable filter (AOTF) in an imaging spectrometer. An AOTF is a solid state electronically tunable spectral bandpass filter which operates on the principle of acousto-optic interaction in an anisotropic medium. Several features of AOTFs make them attractive as a new generation of wavelength sorters for airborne/spaceborne imaging spectrometers. They are fast devices providing electronic tuning in microseconds. They have a relatively wide wavelength range of operation. They can provide a large throughput. They have high resolution. They can be operated in a sequential, random and multi-wavelength access modes. They are compact, rugged and lightweight in construction and have an all solid state structure without moving parts. In addition, AOTFs can operate from visible to infrared wavelengths with spectral resolutions $$\frac{\lambda}{\Delta \lambda}$$

ranging from approximately $10^2$ to $10^4$. Thus, the AOTF is suitable for observations of detailed spectral signatures on earth and planetary surfaces. Furthermore, because of diffraction in an anisotropic medium, there are two diffracted monochromatic beams with polarization orthogonal to each other. Therefore, the AOTF provides a unique capability for measuring spectral, spatial and polarimetric properties of the incoming light, simultaneously with a single instrument.

The use of an AOTF for spectroscopic applications per se, is not new. The following U.S. Patents describe the use of an AOTF in a spectroscopic application.

U.S. Pat. No. 4,883,963 to Kemeny et al is directed to a spectrometer having an acousto-optic tunable filter with programmable rapid random wavelength access for analyzing changing or moving samples of solid or liquid material. The system has the AOTF filter and optical system including polarizing elements, fiber optics for remote detection, if necessary, and control electronics in a computer. The detector however is a semiconductor, not a CCD and the disclosure is not directed to an imaging spectrometer.

U.S. Pat. No. 4,663,961 to Nelson et al is directed to a system for remote chemical analysis using an AOTF. The system has an AOTF, a microcomputer for control and data handling, an optical system with a fiber optics cable for remote use. The detector is lead selenide, not a CCD and there is no reference to imaging.

U.S. Pat. No. 4,622,845 to Ryan et al is directed to a portable system for detecting and measurement of gases using an AOTF. The portable system uses the AOTF, data reduction and control, and a photo acoustic detector. The acoustic detector is only useful for gas analysis and not for imaging.

U.S. Pat. No. 4,652,756 to Ryan et al is directed to an automated AOTF analyzing system for monitoring stack emissions. The system has an optical system, AOTF optics and detector, but no polarizing elements. Discrimination against extraneous radiation is provided by electronics with a microcomputer operating the AOTF in a pulsed mode. The system could be used for solid or liquid analysis but not for imaging.

U.S. Pat. No. 4,490,845 to Steinbruegge et al is directed to an automated IR analyzer using an AOTF. The system comprises two major sub-systems, optics and electronics and is a broadband solid state spectrometer adapted for gases. The optic sub-system has an AOTF detector and polarizing elements. The electronic sub-system has a microcomputer and control electronics. This system, directed to gas analysis, could be used on solid state or liquid samples but not for imaging.

The following non-patent prior art references also disclose relevant subject matter:

1. "Acousto-Optic Devices and Applications" by I. C. Chang, IEEE Transactions On Sonics and Ultrasonics, Vol. SU-23, No. 1, January 1976;
2. "Tunable Acousto-Optic Filters: An Overview" by I. C. Chang, Optical Engineering, Vol. 16, No. 5, September/October 1977;
3. "Acousto-Optic Image Filtering" by I. B. Belikov et al, Soviet Tech. Phys. Lett. 10(10), October 1984;
4. "Rapid Scanning Fluorescence Spectroscopy Using an Acousto-Optic Tunable Filter" by Ira Kurtz et al, Rev. Sci. Instrum., 58(11), November 1987.

SUMMARY OF THE INVENTION

The present invention comprises a multi-spectral imaging instrument using an acousto-optic tunable filter as a high resolution and fast programmable bandpass filter. Such a sensor provides advantages of real-time operation, observational flexibility and measurements of spectral, spatial and polarization information using a single instrument which is compact and which has a solid state structure without moving parts. An AOTF-based imaging spectrometer offers several advantages over imaging spectrometers utilizing dispersive devices such as gratings. The ability to electronically set the bandpass wavelength of an AOTF to any desired value in its wide tuning range, provides significant observational flexibility. This allows observations to be tailored in real-time to perform desired experiments and to collect required data only. This flexibility enables the instrument to address a wide range of objectives and permits the observational parameters to be modified as new objectives are developed, such as in flight or in other situations in which only remote control is possible. Consequently, in applications involving airborne/-spaceborne imaging spectroscopy, the imaging spectrometer of the present invention can be optimized to obtain needed scientific data with minimal resources.

In a preferred embodiment of the invention disclosed herein, a camera zoom lens is used as the input lens. A $TeO_2$ AOTF and a relay lens are placed at selected distances behind the back focal plane of the input lens, respectively. A charge coupled device (CCD) camera, which comprises a camera, camera zoom lens and CCD detector is placed at a selected distance behind the relay lens. An RF signal generator is used to drive the AOTF. The operations of multi-spectral image acquisition, data processing storage and spectogram display are controlled by a computer, such as an IBM PC. Two embodiments of the invention are disclosed herein. One operates in the visible/near-infrared domain, operating in the wavelength range of 0.48 to 0.76 microns. The other embodiment is an infrared configuration which operates in the wavelength range of 1.2 to 2.5 microns However, it will be understood that the specific operating wavelengths of the preferred embodiments disclosed herein are readily altered. The wavelength of operating range is dictated only by the frequency range of the AOTF and the detector. Thus, while tellurium oxide is the preferred acousto-optical material for the visible, near-infrared and mid-infrared spectral regions, there are several other materials that can be used in the far infrared range to 11 microns in wavelength. There are other materials which may be good candidates for an imaging AOTF spectrometer capable of operating in the ultraviolet wavelengths. Accordingly, the specific embodiments of the invention disclosed herein should not be deemed to be limiting of the invention which is more generally related to the advantageous use and application of a real-time AOTF imaging spectrometer having an improved architecture.

OBJECTS OF THE INVENTION

It is therefore a principal object of the present invention to provide a multi-spectral imaging instrument with an improved architecture for real-time spectroscopy that may, for example, be advantageously used in airborne/spaceborne applications for remote observation and sorting of materials.

It is an additional object of the present invention to provide an improved acousto-optic tunable filter imaging spectrometer which permits observations to be tailored in real-time to perform desired experiments and to collect required data only.

It is still an additional object of the present invention to provide a remote sensor in the form of an acousto-optic tunable filter imaging spectrometer capable of real-time observation and employing an optical architecture which provides a fixed intermediate imaging plane with image magnification variability.

It is still an additional object of the present invention to provide a remote, real-time AOTF imaging spectrometer having an improved optical architecture which provides improved image resolution and light throughput efficiency.

BRIEF DESCRIPTION OF THE DRAWINGS

The aforementioned objects and advantages of the present invention, as well as additional objects and advantages thereof, will be more fully understood hereinafter as a result of a detailed description of preferred embodiments of the invention when taken in conjunction with the following drawings in which.

DETAILED DESCRIPTION OF PREFERRED EMBODIMENTS

Figure 1:
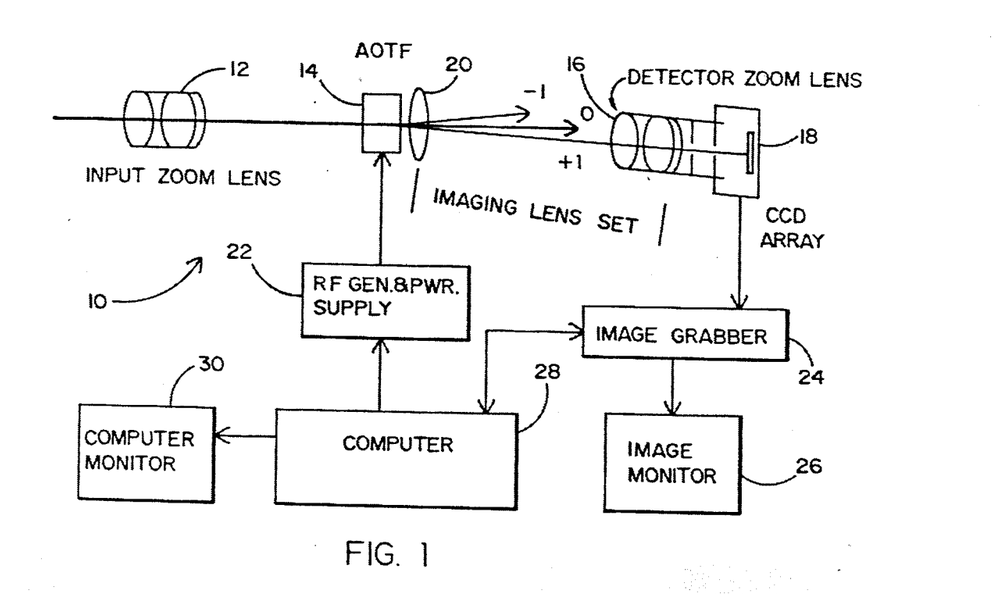
FIG. 1 is a block diagram of an AOTF imaging spectrometer of the present invention.

As shown in FIG. 1, the optical system 10 of the present invention comprises foreoptics 12, the AOTF 14, imaging optics 16 and a charge coupled device (CCD) camera 18. An ordinary camera zoom lens is used for the foreoptics. A field lens 20 is placed behind the AOTF. The combination of the field lens 20 and the camera lens 12 generates the diffracted image at the CCD detector array 18. Two types of CCD cameras have been used in the embodiment of FIG. 1, namely an electrically-cooled integrating CCD camera for precision measurements in the laboratory and an ordinary CCD video camera for real-time observations. The system further comprises an RF generator and power supply 22, an image grabber 24 and monitor 26 and a computer 28 such as a IBM 386 PC computer for control and data acquisition. A monitor 30 is also provided.

Figure 3:
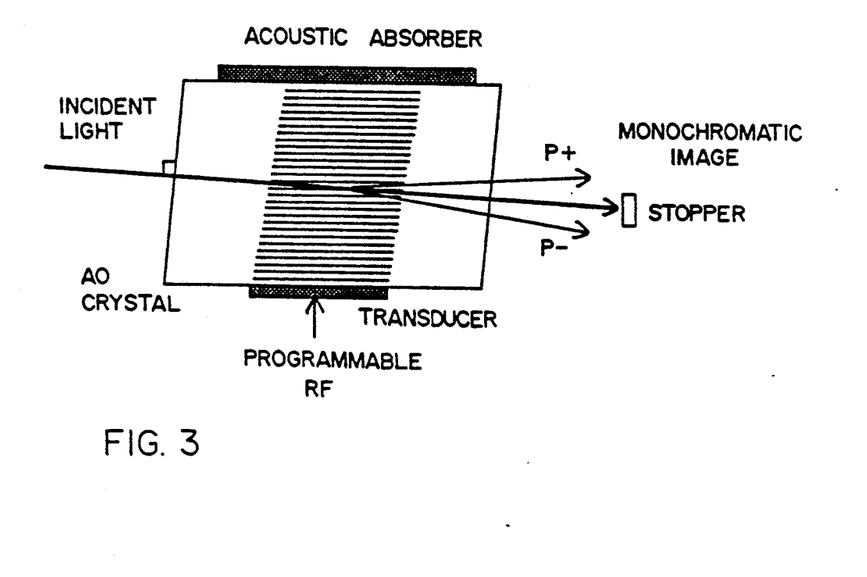
FIG. 3 is a schematic illustration of a non-collinear AOTF.

FIG. 3 illustrates schematically, a non-collinear AOTF. It comprises a birefringent crystal to which one or several piezoelectric transducers are bonded. When an RF signal is applied, acoustic waves are generated and launched into the crystal. The propagating acoustic waves produce a periodic modulation of index of refraction. This provides a moving phase grating which diffracts portions of an incident light beam. For a fixed acoustic frequency and a sufficiently long interaction length, only a limited band of optical frequencies can approximately satisfy the phase-matching condition and be collectively diffracted. As the RF frequency is changed, the center of optical bandpass is changed accordingly because the phase-matching condition must be satisfied. This description of an acousto-optic spectral filtering mechanism applies to both an isotropic medium and to a birefringent crystal However, in an isotropic medium the filtering action is extremely sensitive to the angle of light incidence and is thus useable only for collimated light. This is one reason why isotropic Bragg diffraction, which has been observed over fifty years, cannot be used for imaging spectrometry.

Figure 4:
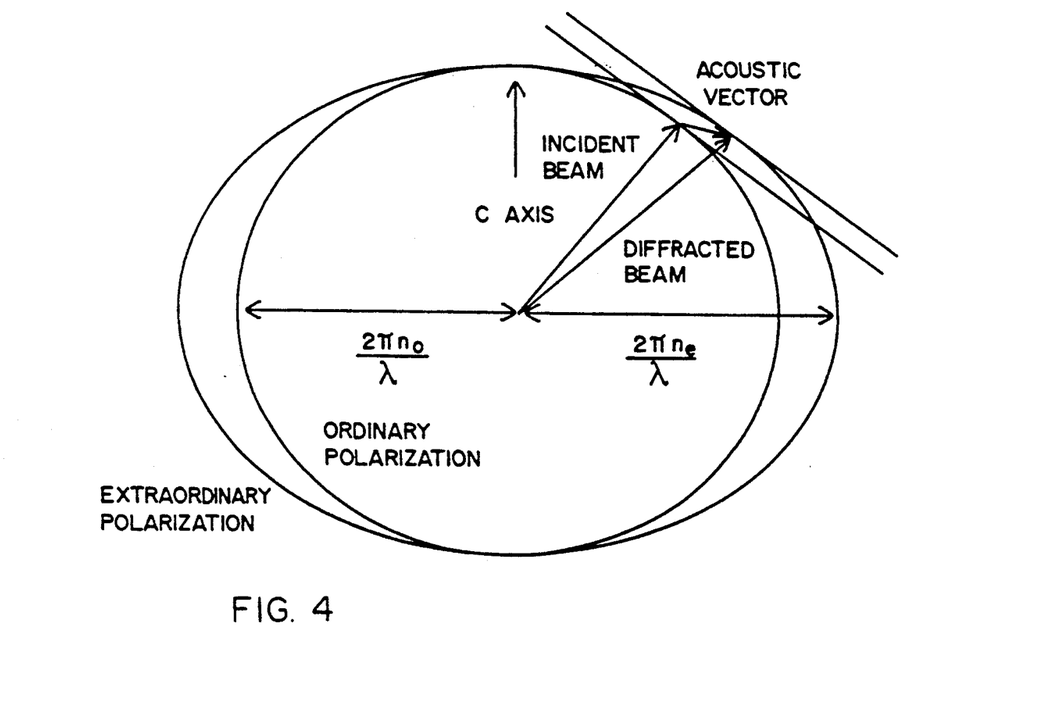
FIG. 4 is a wave vector diagram for a non-collinear AOTF.

In an anisotropic medium such as a uniaxial crystal, there are two distinct refraction index surfaces, one for the ordinarily polarized light and the other for the extraordinarily polarized light. In this case, the acoustic wave may couple incident polarized light into the orthogonal polarization. For this birefringent diffraction, it is possible to satisfy the phase-matching condition for incident light having a range of incidence angles. The basic concept is illustrated by the wave vector diagram of FIG. 4 for acousto-optic diffraction in a uniaxial crystal. Referring to FIG. 4, it will be seen that the acoustic wave vector is chosen so that the tangents to the incident and diffracted light wave vector surfaces are parallel. When this parallel tangent condition is met, the acousto-optic diffraction becomes relatively insensitive to the angle of light incidence, a process that is referred to as noncritical phase-matching. If the incident beam is unpolarized, there will be two orthogonally polarized diffracted beams exiting at the opposite sides of the undiffracted beam, as illustrated in FIG. 4. This provides opportunities to measure polarization of incident light. Tellurium oxide (TeO$_2$) is the preferred acousto-optic material for the visible, near-infrared and mid-infrared spectral regions (0.4–5.0 microns) because of the availability of high quality crystals. There are several other materials that can be used in the far-infrared range, such as to 11 microns in wavelength. Among them, Tl$_3$AsSe$_3$ is the one which is commercially available. For ultraviolet wavelengths, quartz is a good candidate.

Figure 5:
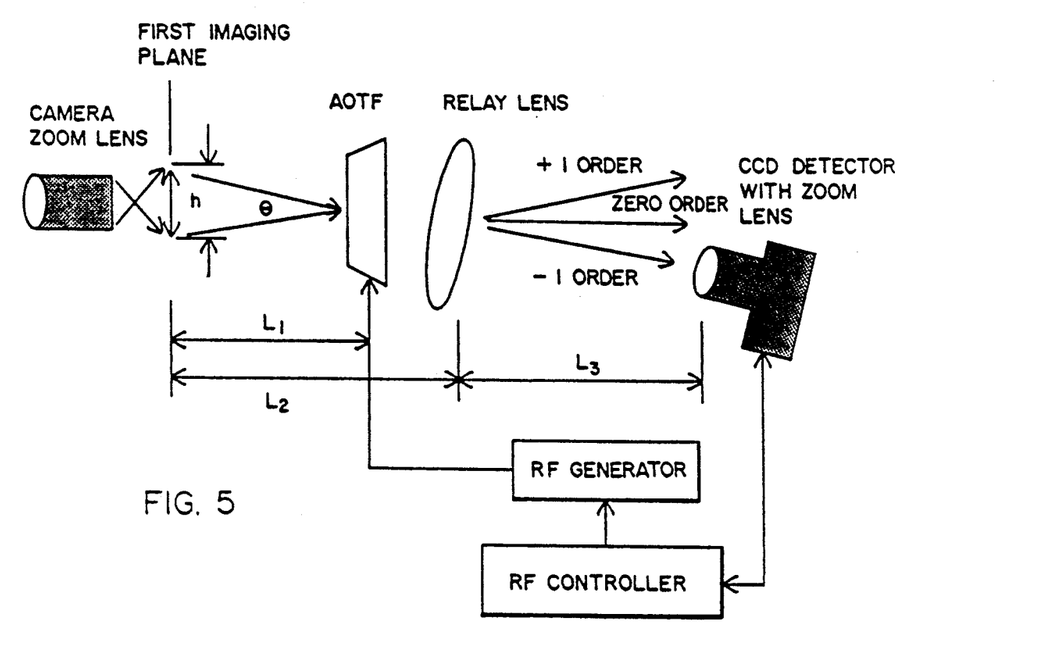
FIG. 5 is a system schematic diagram of an AOTF imaging spectrometer actually reduced to practice.

FIG. 5 illustrates a schematic representation of the imaging spectrometer of the present invention, wherein a camera zoom lens is used at the input and a tellurium oxide AOTF and a relay lens are placed at distances L1 and L2 behind the back focal point of the input lens respectively The CCD camera, which consists of a camera, camera zoom lens and a CCD detector, in place at a distance L3, behind the relay lens. An RF signal generator is used to drive the AOTF and the entire operation of multi-spectral image acquisition, data processing, storage and spectrogram display are controlled by an IBM PC compatible computer.

In order to understand the principle of operation of the AOTF imaging spectrometer, one may first analyze its system impulse response. Because the input objects to be studied are usually located at a distance that is much longer than the focal length of the input camera zoom lens, the object images are focused very closely to the back focal plane of the input lens. Thus, for simplicity of analysis, we define the back focal plane of the input lens as the first imaging plane and perform the system impulse response analysis by treating the first imaging plane as the input image plane. To obtain the impulse response, we place a point monochromatic light source in the first imaging plane. Light wavefront W1 emanating from this point source and impinging upon the AOTF can be expressed as:

$$W_1 = \exp\left[\frac{i\pi(x^2 + y^2)}{\lambda L_1}\right] \quad (1)$$

where L1 is the distance between the source plane and the AOTF plane. Equation 1 is obtained using Fresnel diffraction approach with a paraxial assumption, and $\lambda$ is the wavelength of the light source. The light diffraction taking place within an AOTF is determined by the momentum matching between the light and the acoustic wave vectors. A specific wavelength can be effectively diffracted by the AOTF with respect to a corresponding driving RF signal. In general, the AOTF can be represented by a one dimensional volume grating. If the input light beams are randomly polarized, then output light beams exit from the AOTF comprised of three components. As shown in FIG. 5, the ordinary beams are diffracted downward and form the $-1$ order. The extraordinary beams are diffracted upward and form the $+1$ order. The undiffracted light is the 0 order. We shall focus only on the ordinary beams and thus perform our analysis with respect to the $-1$ order of diffracted beams. The angle of diffraction with respect to the $-1$ order is $\theta$. Because the refractive index of Tellurium oxide crystal is wavelength dependent, $\theta$ measured in air, is also a function of the wavelength. Light wavefront W2 immediately exiting the AOTF, thus can be expressed as:

$$W_2 = \exp\left(\frac{i\pi[(x - L_1\theta)^2 + y^2]}{\lambda L_1}\right) \quad (2)$$

A relay lens is placed behind the AOTF at a distance L2 from the first imaging plane. The light wavefront W3 incident upon the lens is:

$$W_3 = \exp\left(\frac{i\pi[(x - L_1\theta)^2 + y^2]}{\lambda L_2}\right) \quad (3)$$

Figure 6:
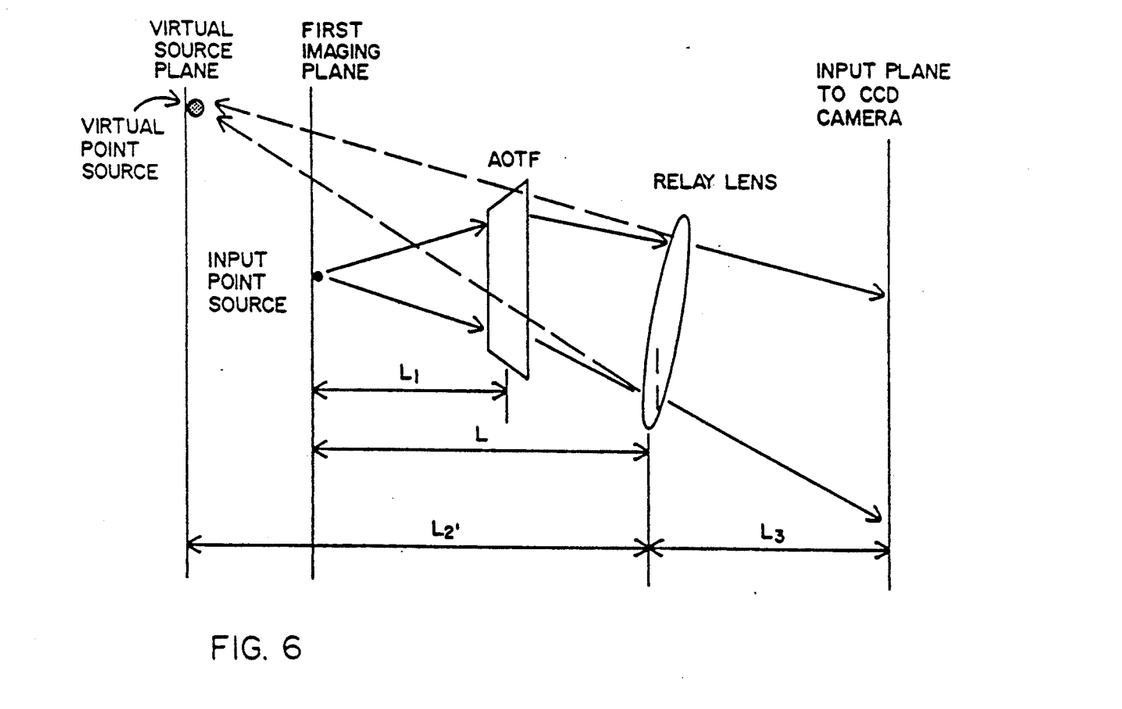
FIG. 6 is an analytical drawing of the imaging spectrometer of FIG. 5 that is used to define the system impulse response thereof.

After some simple derivations, it can be shown that light wavefront W4, immediately exiting from the lens can be written as:

$$W_4 = \exp\left\{\frac{i\pi\left[\left(x - \left(\frac{fL_1\theta}{f - L_2}\right)\right)^2 + y^2\right]}{\lambda\left(\frac{L_2 f}{f - L_2}\right)}\right\} \quad (4)$$

where f is the focal length of the relay lens. From equation 4, we see that when the separation distance L2 between the first imaging plane and the relay lens is less than the focal length f, W4 comprises a diverging wavefront which can be viewed as if it is emanating from a point source located at a distance (L2f)/(f−L2) away from the relay lens toward the first imaging plane. A lateral shift of this point source of a distance (fL1θ)/(f−L2) also occurs due to the diffraction by the AOTF. For overall imaging analysis, this imaging system can be simplified, and as shown in FIG. 6, the input object obtained by the input zoom lens can be treated as being at a distance of L0 away from the CCD camera and L0 can be written as:

$$L_0 = [L_2 f/(f - L_2)] + L_3, \quad (5)$$

where L3 is the distance between the relay lens and the CCD camera. From equation 4 and equation 5, we see that the virtual object distance L0 can be chosen to be longer than the length L2 plus L3 of the AOTF system. Equation 5 provides a simple analysis of the imaging distance design. Distances L2 and L3 can be separately adjusted, such that an output image of appropriate magnification can be obtained using the zoom lens mounted on the CCD detector. A compact system which is less than two feet in length has been built using this design. This design offers great flexibility in selecting the system parameters, as well as ease in system alignment.

One of the important approaches utilized in this optical system design is that the AOTF is placed at an appropriate distance behind the input imaging plane. This placement reduces the adverse affect caused by non-uniformity in diffraction efficiency across the AOTF aperture. Moreover, the undiffracted 0 order and the two first order output images are effectively separated without the need of a spatial filter. The diffraction angle $\theta$ of the light beam exiting from the AOTF is wavelength dependent as a result of the K space moment matching and the Snell refraction between the $TeO_2$ crystal and air. The equivalent lateral shift of the input object, viewed by the CCD camera is shown in equation 3 as $D = (f L_1 \theta)/(f - L_2)$. The equivalent system schematic of the AOTF imaging system of FIG. 5 is shown in FIG. 6. Because the diffraction angle $\theta$ is wavelength dependent, the lateral shift of the object is also varied with the tuned spectral band wavelength. This results in spectral shift in the output image plane.

The field of view (FOV) of the AOTF imaging spectrometer of FIG. 5 is mainly restricted to the azimuthal angular aperture of the AOTF. As the field of view exceeds the angular aperture of the AOTF, the bandwidth of the central spectral passband will be adversely increased and blur the output image. As shown in FIG. 5, the FOV of the AOTF imaging spectrometer shown therein is determined by the ratio of H/L1 where H is the maximum lateral extension of the image over the first imaging plane and L1 is the separation between the first imaging plane and the AOTF plane. Thus, the FOV of the AOTF imaging spectrometer of FIG. 5 can be precisely determined by the separation distance between the first imaging plane and the AOTF plane. This distance can also easily be adjusted to match the azimuthal angular aperture of a specific AOTF.

In a first embodiment of the present invention, suitable for use at visible/near-infrared wavelengths, the input lens is a 100-300 millimeter camera zoom lens. The first imaging plane is located at the back focal plane of the input lens. The AOTF is made of Tellurium oxide crystal with an 11 degree crystal cut. It has an aperture of ½ inch by ½ inch and a spectral bandwidth of 0.45 to 0.76 microns. The RF tuning frequency is from 50 to 90 MHz. and typical operation power is about 150 milliwatts or less. The maximum driving RF power is 500 milliwatts, however, to maintain a high main-to-side lobe-ratio, a low driving power is used. In order to obtain a uniform output image, an aperture is placed over the first imaging plane as shown in FIG. 5, such that the maximum lateral image width D is restricted to be 20 millimeters. The separation distance L1, between the first imaging plane and the AOTF is about 100 millimeters. The resultant azimuthal angle $\theta$ is about 11.3 degrees in air and corresponds to 5.0 degrees and 4.6 degrees within the crystal, respectively. These angles are within the limit of the input angle of the AOTF and thus excellent spectral resolution is obtained. The separation distance L2 is about 150 millimeters. The focal length of the relay lens is 200 millimeters. With reference to equation 3, the virtual imaging plane is 600 millimeters away from the relay lens. The distance between the relay lens and the CCD camera is 400 millimeters. Thus, the input image is projected at a distance of about 1000 millimeters from the CCD camera. The 210 millimeter zoom lens mounted on the CCD camera has a minimum imaging distance of 750 millimeters. With the aid of the relay lens, the input object image is easily recorded by the CCD camera. The diffraction angle of the first order light beam varies from 6.95 degrees to 7.30 degrees. The corresponding lateral shift of the object varies from 60.6 millimeters to 63.7 millimeters in the input plane. This lateral separation is adequate for the separation of the $-1$ order output image from the 0 order image.

Experiments to characterize the visible/near-infrared system of FIG. 5 have been carried out. The maximum observed spectral shift across the imaging plane for several laser lines from an Argon laser and a helium neon laser was less than 1 nm; about 25% of the bandpass width, illustrating good spectral accuracy. The bandpass has observable side lobes at each side of the main peak as expected from theory. The larger side-lobe intensity is about 7% of that of the main peak which can be substantially reduced if a proper apodization is applied to control the acousto-optic interaction profile in the AOTF. There is no observable bandpass-width change across the image plane. The spectral shift of the AOTF due to temperature variation was measured to be 0.067 nm per degree Celsius, which is extremely small.

Figure 2:
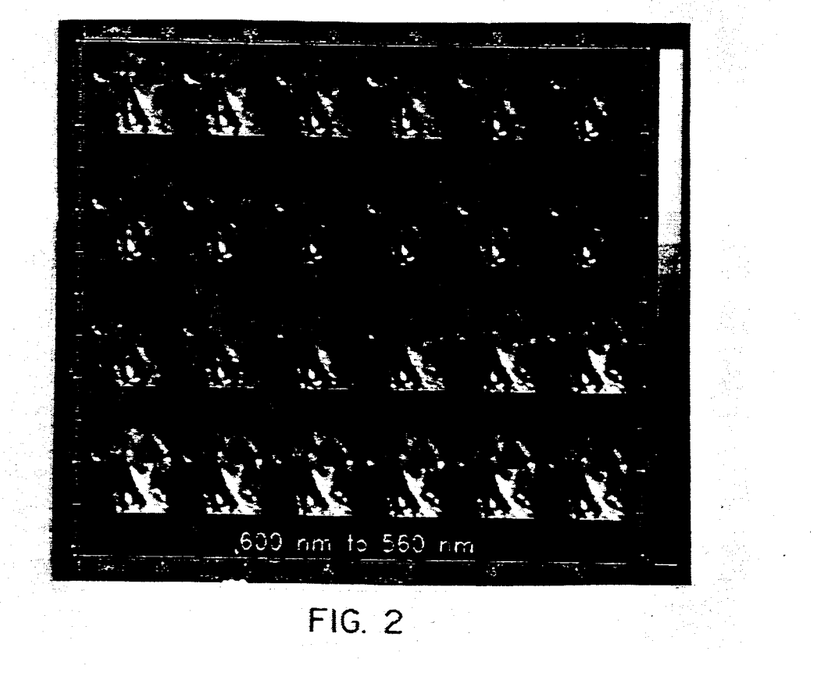
FIG. 2 is a photographic figure of 24 image frames taken at sequentially stepped wavelengths of the AOTF.
Figure 7:
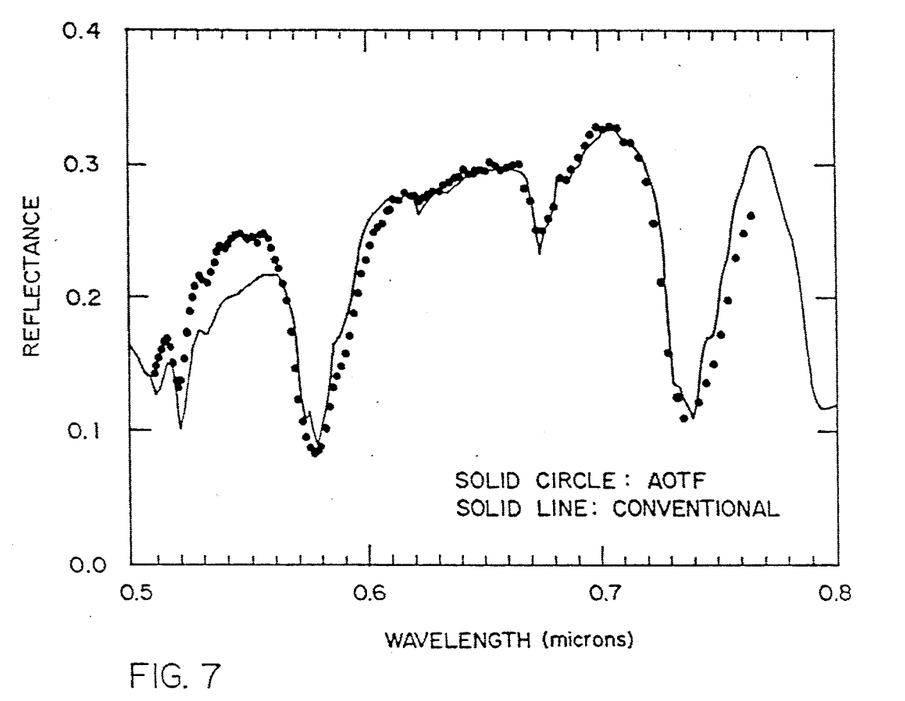
FIG. 7 is an AOTF spectral scan graph taken in the wavelength range of 0.5 to 0.77 microns.

A Bastnaesite rock sample was used in the experiment. This mineral contains neodymium and samarium fluorocarbonate in a silica matrix. The rock was illuminated by a sunlamp during the measurement. FIG. 2 shows a series of spectrally resolved images of a portion of the Bastnaesite rock. There are 24 frames in FIG. 2, representing a wavelength step of approximately 3 nm from 710 nm to 783 nm. The area richest in neodymium (right side of each frame) changes from light to dark, as the wavelength is stepped through a neodymium absorption band at 744 nm. FIG. 7 illustrates a reflectance spectrum of the Bastnaesite rock obtained, using the AOTF imaging spectrometer of the present invention. FIG. 7 also shows a spectrum of a similar sample obtained using a conventional spectrometer for comparison. The similarity of the two spectra illustrates the capability of using the AOTF imaging spectrometer for geological feature detection.

Figure 8:
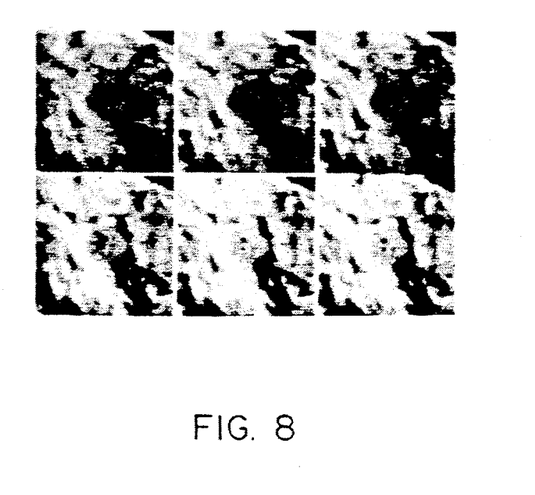
FIG. 8 is a collection of six photographic images of a small surface area of a rock sample, taken at six different wavelengths with the invention.

Insertion of an optical fiber bundle in an AOTF spectrometer between the fore-optics and the AOTF, can provide powerful observation flexibility through a three-dimensional rotatable and adaptable optical head. This can be an important improvement for some space missions, such as the Mars Rover. The visible/near-infrared system of FIG. 5 was modified to accept an optical bundle containing 1000 by 800 10-micron-fused silica fibers. Good quality spectral images were obtained thus illustrating the feasibility of coupling a highly manipulative fore optic head to an AOTF imaging spectrometer through a fiber bundle. FIG. 8 illustrates six images of a small surface area at the boundary between an Nd-rich and an Nd-deficient area of the Bastnaesite rock sample observed through the optical fiber bundle. These images, taken at wavelengths within the 0.58 micron absorption band, show clearly the Nd-rich area, while those taken at wavelengths away from the absorption band do not.

Figure 9:
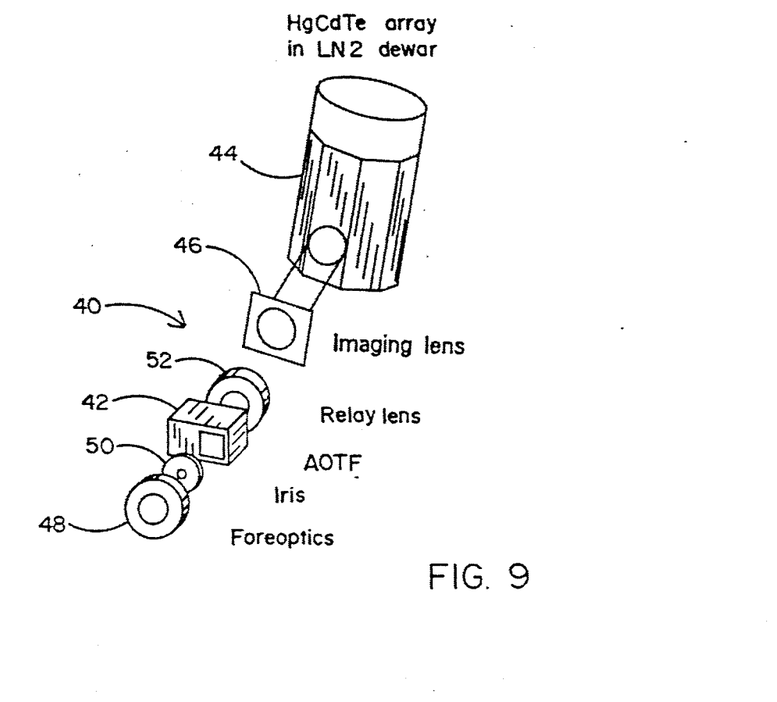
FIG. 9 is a schematic diagram of a 1.2 to 2.5 micron wavelength infrared AOTF imaging spectrometer that has been reduced to practice.

The optical system architecture of the second embodiment of the invention shown herein, namely the infrared wavelength system 40, is seen in FIG. 9. It is essentially the same as that of the visible/near-infrared configuration of FIG. 5, except that a liquid nitrogen-cooled HgCdTe detector array 44 and a set of ZnSe lenses 46 are used. Foreoptics 48, iris 50 and relay lens 52 serve the same purpose described previously for the embodiment of FIG. 1. The Tellurium oxide AOTF 42 in the system of FIG. 9 is designed for operation in the wavelength range of 1.2 to 2.4 microns. The bandpass of the AOTF 42 is 10 nm at 1.8 microns. The control and data acquisition apparatus are similar to those used in the visible/near-infrared embodiment of FIG. 5.

Figure 10:
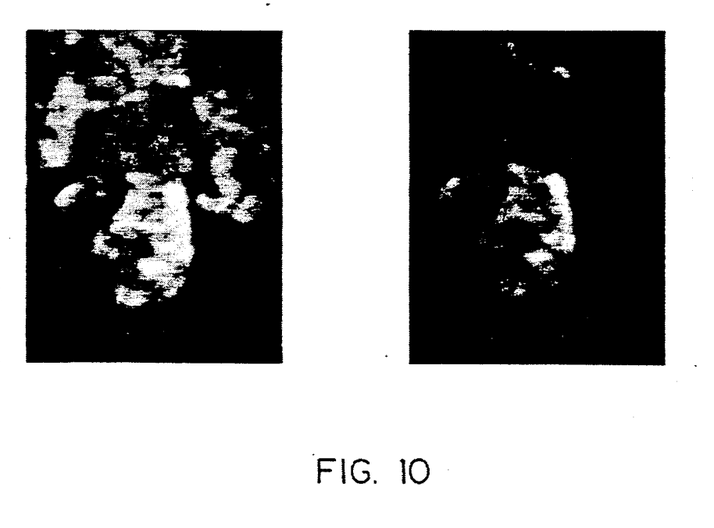
FIG. 10 comprises two photographic images of a rock sample taken at two different infrared wavelengths, namely 2.2 and 2.3 microns respectively.

FIG. 10 illustrates two photographic images taken with the AOTF imaging spectrometer of FIG. 9. The images are of a part of the Bastnaesite rock and a small sandstone at the lower front as a reference. The image at the left was taken at 2.2 microns, where both the Bastnaesite rock and the sandstone had roughly similar reflectance and their surface structures are both observable. However, the image at the right of FIG. 10 was taken at 2.3 microns. The rock surface is much darker because the rock has an absorption band at this wavelength, due to its carbonate radical. The sandstone has no absorption band at this wavelength, so its surface is still observable at the 2.3 micron wavelength.

Figure 11:
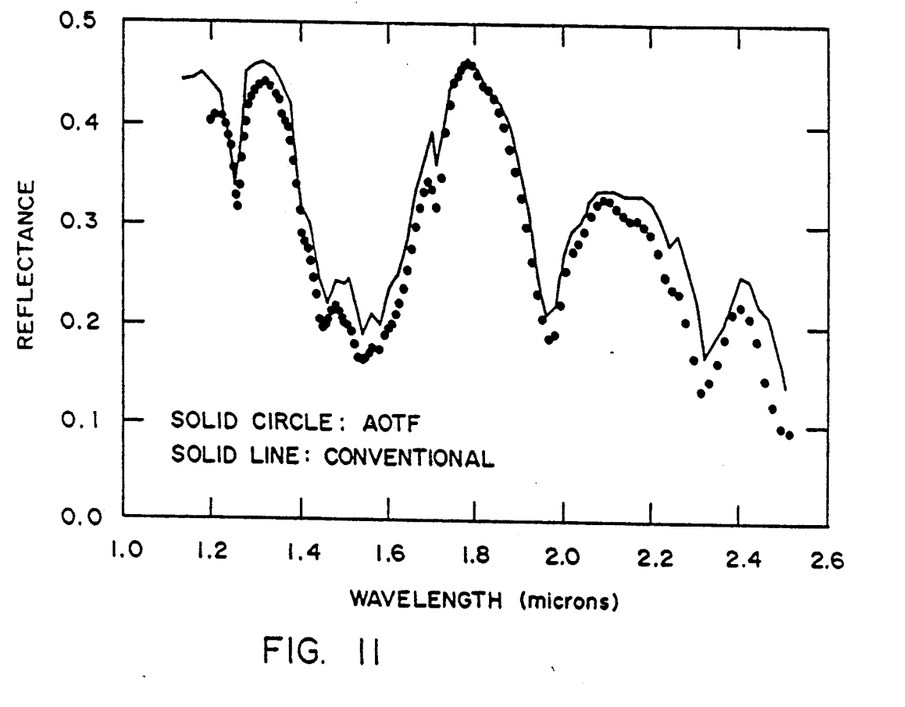
FIG. 11 is an AOTF infrared reflective spectral scan graph taken with the second embodiment of the invention.

FIG. 11 illustrates the infrared reflective spectral data of a Bastnaesite sample taken using the infrared embodiment of the invention shown in FIG. 9. FIG. 11 compares that data with data of a similar rock taken with a conventional spectrometer. All of the absorption peaks observed by the two techniques are the same. The reflectance values measured over the wavelength range are also approximately the same. These results demonstrate the capability of using the infrared AOTF imaging spectrometer to identify and map mineral contents.

APPLICATIONS

The real-time imaging spectroscopic capability of the present invention can be advantageously used in a number of diverse applications. By way of example, as previously noted, the present invention could find highly advantageous use in a spaceborne application such as the Mars Lander. The present invention could be used in the Mars Lander to detect and identify the mineral content of adjacent materials to permit intelligent selection of samples to be returned to the earth. However, the applications for the present invention include non-spaceborne applications as well. For example, a compactly packaged, highly reliable, real-time imaging spectrometer can be highly advantageous for military surveillance purposes, such as for improved detection of camouflaged targets. In addition, the present invention could find highly advantageous applications in the medical field such as, for example, for use at the distal tip portion of catheter tubes to aid in the observation of certain forms of tissue. The present invention could also find advantageous application for industrial sorting purposes, such as where products which differ in color, even to a slight degree, need to be separated from one another in an automatic process.

The present invention can also be advantageously used in both terrestrial and spaceborne astronomical applications where, for example, narrow band red shift measurements can be made using the frequency selection characteristics of the present invention. An imaging spectrometer of the present invention could also find advantageous use in environmental protection applications, such as in the real-time monitoring of environmental conditions such as ocean pollution or leakage of nuclear waste and the like. Thus, while the present invention was principally designed for airborne/spaceborne applications such as the Mars Rover program and the like, it will be understood that it provides a new basic instrument for observation and measurement of spectral, spatial and polarization information, all in real-time, using a single, compact, solid state instrument without moving parts that has advantageous use in a number of highly diverse fields.

It will be understood that the present invention provides certain highly advantageous architectural improvements which result in superior performance as compared to known prior art AOTF imaging spectrometers. One such improvement is the use of a single input zoom lens to produce an image of the input object in an intermediate plane whereby image magnification can be varied without varying the image plane. This feature can be especially advantageous in simplifying remote systems such as for spaceborne applications. Another such improvement is the placement of the AOTF in front of a relay lens where it is closer to the intermediate imaging plane to provide improved image resolution and improved light throughput efficiency. Still another such improvement comprises mounting a camera zoom lens directly on the image detector. This obviates the use of a spatial filter near the detector and precludes saturation of the detector from ambient light. It also reduces the complexity of system alignment.

Those having skill in the art to which the present invention pertains, will now as a result of the applicants' teaching herein, perceive various modifications and additions which may be made to the invention. By way of example, other operational wavelengths facilitated by the use of different AOTF materials and different detecting devices other than those disclosed specifically herein, may be readily utilized. Accordingly, all such modifications and additions are deemed to be within the scope of the invention, which is to be limited only by the claims appended hereto and their equivalents.

We claim:

1. An imaging spectrometer comprising an acousto-optic tunable filter of the type having an optical wavelength passband which is dependent on the selected frequency of an RF signal applied to said filter;
   input optics forming an intermediate image plane for directing incident image light into said filter within a field of view of said filter;
   a detector having an image plane for receiving image light passed by said filter;
   output optics positioned between said filter and said detector for producing a focussed image on said detector image plane;
   an RF signal source for applying said RF signal to said filter; and means for controlling said source for generating an RF signal having said selected frequency;

wherein said filter optical wavelength passband is in the range of 0.4 to 5.0 microns.

2. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said selected frequency of said RF signal is in the range of 50 to 90 MHz.

3. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said controlling means comprises a computer.

4. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said detector comprises a charge-coupled device.

5. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said detector comprises a charge-coupled device detector within a CCD camera.

6. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said detector comprises a HgCdTe detector array.

7. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said output optics are positioned relative to said filter to receive only one polarization of light therefrom without the use of a spatial filter at said detector.

8. An imaging spectrometer comprising an acousto-optic tunable filter of the type having an optical wavelength passband which is dependent on the selected frequency of an RF signal applied to said filter;

input optics forming an intermediate image plane for directing incident image light into said filter within a field of view of said filter;

a detector having an image plane for receiving image light passed by said filter;

output optics positioned between said filter and said detector for producing a focussed image on said detector image plane;

an RF signal source for applying said RF signal to said filter; and means for controlling said source for generating an RF signal having said selected frequency;

wherein said output optics comprises a zoom lens mounted directly on said detector.

9. An imaging spectrometer comprising foreoptics for collecting light incident on said spectrometer;

an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said AOTF optical wavelength passband is in the range of 0.4 to 5.0 microns.

10. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said frequency of said RF signal is in the range of 50 to 90 MHz.

11. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said controlling means comprises a computer.

12. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said detector comprises a charge-coupled device.

13. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said detector comprises a charge-coupled device detector within a CCD camera.

14. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said detector comprises a HgCdTe detector array.

15. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said imaging lenses are positioned relative to said AOTF to receive only one polarization of light therefrom without the use of a spatial filter at said detector.

16. An imaging spectrometer comprising foreoptics for collecting light incident on said spectrometer;
an AOTF positioned substantially at an intermediate imaging plane relative to said foreoptics for receiving said collected light;
imaging lenses for focussing an image passed by said AOTF;
a detector for detecting said focussed image;
an RF signal generator connected to said AOTF for altering the optical passband thereof; and
means for controlling the frequency of said RF signal generator for selecting the optical wavelength of said AOTF;
wherein said imaging lenses comprise a zoom lens mounted directly to said detector.

* * * * *